(12) United States Patent
Sitruk-Ware et al.

(10) Patent No.: US 9,364,488 B2
(45) Date of Patent: Jun. 14, 2016

(54) MYELIN REGENERATION WITH ANDROGENS

(75) Inventors: Regine Sitruk-Ware, New York, NY (US); Michael Maria Helmut Schumacher, Kremlin-Bicêtre (FR); Abdelmouman Ghoumari, Antony (FR); Said Ghandour, Strasbourg (FR); Rashad Hussain, Denver, CO (US); Bartosz Bielecki, Kremlin-Bicêtre (FR)

(73) Assignee: The Population Council, Inc., New York, NY (US)

( * ) Notice: Subject to any disclaimer, the term of this patent is extended or adjusted under 35 U.S.C. 154(b) by 43 days.

(21) Appl. No.: 14/005,690

(22) PCT Filed: Mar. 22, 2012

(86) PCT No.: PCT/US2012/030041
§ 371 (c)(1),
(2), (4) Date: Sep. 17, 2013

(87) PCT Pub. No.: WO2012/129365
PCT Pub. Date: Sep. 27, 2012

(65) Prior Publication Data
US 2014/0011791 A1  Jan. 9, 2014

Related U.S. Application Data

(60) Provisional application No. 61/466,252, filed on Mar. 22, 2011.

(51) Int. Cl.
| | | |
|---|---|---|
| A61K 31/56 | (2006.01) |
| A61K 31/573 | (2006.01) |
| A61K 31/565 | (2006.01) |
| A61K 31/568 | (2006.01) |
| A61K 31/57 | (2006.01) |

(52) U.S. Cl.
CPC ............. *A61K 31/573* (2013.01); *A61K 31/565* (2013.01); *A61K 31/568* (2013.01); *A61K 31/57* (2013.01)

(58) Field of Classification Search
USPC ................................................ 514/181, 178
See application file for complete search history.

(56) References Cited

U.S. PATENT DOCUMENTS

| 3,710,795 A | 1/1973 | Higuchi et al. |
| 6,767,902 B2 | 7/2004 | Moo-Young |
| 2005/0182105 A1 | 8/2005 | Nirschl et al. |

FOREIGN PATENT DOCUMENTS

| JP | 2005-518438 A | 6/2005 |
| JP | 2009-510084 A | 3/2009 |
| JP | 2010-248250 A | 11/2010 |
| WO | 03/072110 A1 | 9/2003 |
| WO | 2007/038636 A2 | 4/2007 |
| WO | 2011049948 A2 | 4/2011 |

OTHER PUBLICATIONS

Sicotte et. al. (Arch. Neurol. (2007) 64:683-688).*
Palaszynsky (Journal of Neuroimmunology (2004) 146144-152).*
Kumar et. al. (Endocrinolgy (1992) 130:3677-3683).*
Schumacher et. al. (Current Opinion in Pharmacology (2008) 8:740-746).*
Anderson et al., "7a-Methyl-19-Nostestosterone Maintains Sexual Behavior and Mood in Hypogonadal Men", The Journal of Clinical Endocrinology & Metabolism, Oct. 1999, vol. 84, No. 10, pp. 3556-3562.
Chien et al., "Controlled drug release from polymeric devices I: Technique for rapid in Vitro release studies", Journal of Pharmaceutical Sciences, vol. 63, No. 3, Mar. 1974.
Confavreux C, Aimard G, Devic M. Course and prognosis of multiple sclerosis assessed by the computerized data processing of 349 patients. Brain 1980;103(2) :281-300.
Confavreux C, Vukusic S. Natural history of multiple sclerosis: a unifying concept. Brain 2006;129(Pt 3) :606-16.
Confavreux et al., "Age at disability milestones in multiple sclerosis", Brain (2006), 129, 595-605.
Dubois-Dalq et al., "The neurobiology of X-linked adrenoleukodystrophy, a demyelinating peroxisomal disorder", TINS vol. 22, No. 1, 1999.
Dutta R, Trapp BD, Pathogenesis of axonal and neuronal damage in multiple sclerosis. Neurology 2007;68 (22 Suppl 3) :S22-S31.
El-Etr Martine et al: :"Hormonal influences in multiple sclerosis: new therapeutic benefits for steroids.", Maturitas Jan. 2011 LNKD-PUBMED:21035281, vol. 68, No. 1, Jan. 2011, pp. 47-51, XP0027568129.
Franklin et al., "Remyelination in the CNS: from biology to therapy", Nature Reviews / Neuroscience, vol. 9, Nov. 2008, pp. 839-855.
Ghoumari A et al: "Progestins induce myelination and remyelination in slice cultures of murine cerebellum", Society for Neuroscience Abstract Viewer and Itinerary Planner, vol. 39, 2009, XP008152898, & 39th Annual Meeting of the Society-for-Neuroscience; Chicago, IL, USA; Oct. 17 -21, 2009. The whole document.
Gold Stefan M et al: "Estrogen and testosterone therapies in multiple sclerosis.", Progress in Brain Research 2009 LNKDPUBMED: 19660668, vol. 175, 2009, pp. 239-251, XP008152791, ISSN: 1875-7855 abstract p. 245, left-hand column, last paragraph -p. 247, left-hand column, last paragraph.

(Continued)

*Primary Examiner* — Marcos Sznaidman
(74) *Attorney, Agent, or Firm* — Lerner, David, Littenberg, Krumholz & Mentlik, LLP

(57) ABSTRACT

Methods for effective remyelination in patients are disclosed comprising treating the patient with an androgen receptor ligand which exerts binding to androgen receptors and elicits androgen-receptor-induced biological responses at a dosage sufficient to induce remyelination. The androgen compound preferably comprises MENT in an androgen targeting both androgen and estrogen receptors, and the methods include combining the androgen compound with a progestin compound in order to provide both contraception in men and treatment for neurodegeneration.

9 Claims, 8 Drawing Sheets

(56) References Cited

OTHER PUBLICATIONS

Intenational Search Report for Application No. PCT/US2012/030041 dated Aug. 13, 2012.
Irvine KA, Blakemore WF. Remyelination protects axons from demyelination-associated axon degeneration. Brain 2008; 131 (Pt 6) :1464-77.
Kornek B, Storch Mk, Weissert R, Wallstroem E, Stefferl A, Olsson T, Linington C, Schmidbauer M, Lassmann H. Multiple sclerosis and chronic autoimmune encephalomyelitis: a comparative quantitative study of axonal injury in active, inactive, and remyelinated lesions. Am.J Pathol. 2000157(1) :267-76.
Kumar et al., "The biological activity of 7a-Methyl-19-Nortestosterone Is Not Amplified in Male Reproductive Tract as is That of Testosterone", Endocrinology 1992, vol. 130, No. 6, pp. 3677-3683.
Melcangi R C et al: "The action of steroid hormones on peripheral myelin proteins: a possible new tool for the rebuilding of myelin?", Journal of Neurocytology May-Jun. 2000 LNKD-PUBMED:11424949, vol. 29, No. 5-6, May 2000, pp. 327-339, XP002678487, ISSN: 0300-4864.
Palaszynski Karen M et al: "Androgens are protective in experimental autoimmune encephalomyelitis: implications for multiple sclerosis", Journal of Neuroimmunology Jan. 2004 LNKD-PUBMED: 14698857, vol. 146, No. 1-2, Jan. 2004, pp. 144-152, XP002678484, ISSN 0165-5728 the whole document.
Partial Search Report for Appplication No. PCT/US2012/030041 dated Jul. 5, 2012.
Patani R, Balaratnam M, Vora A, Reynolds R. Remyelination can be extensive in multiple sclerosis despite a long disease course. Neuropathol.Appl.Neurobiol. 2007;33(3) :277-87.
Patrikios P, Stadelmann C, Kutzelnigg A, Rauschka H, Schmidbauer M, Laursen H, Sorensen PS, Bruck W, Lucchinetti C, Lassmann H. Remyelination is extensive in a subset of multiple sclerosis patients. Brain 2006;129(Pt 12) :3165-72.
Pugliatti M, Rosati G, Carton H, Riise T, Drulovic J, Vecsei L, Milanov I. The epidemiology of multiple sclerosis in Europe. Eur.J. Neurol. 2006;13(7) :700-22.
Sherafat M A et al: "Comparative Study of Local Demyelination and Remyelination Between Male and Castrated Rats' Optic Nerves and Chiasm", Glia, Wiley-Liss, New York, NY, US, vol. 57, No. 13, Oct. 1, 2009, p. S156, XP008152785.
Sicotte Nancy L et al: "Testosterone treatment in multiple sclerosis—A pilot study", Archives of Neurology, vol. 64, No. 5, May 2007, pp. 683-688, XP002678483, ISSN: 00383-9942 the whole document.
Sugiyama et al., "ERb: recent understanding of estrogen signaling", Trends in Endocrimology and Metabolism 21 (2010) 545-552.
Sundaram et al., "7a-Methyl-Nortestosterone (MENT): The Optimal Androgen for Male Contraception", Ann. Med. Apr. 1993, 25(2): 199-205.
U.S. Appl. No. 61/279,320, filed Oct. 19, 2009.
Canadian Office Action for Application No. 2,830,519 dated May 28, 2014.
Hussain, Rashad, "Ro . . . ", 2011, Doctoral thesis in Neuroscience, Paris.
Japanese Office Action for Application No. 2014-501230 dated Dec. 24, 2015.

\* cited by examiner

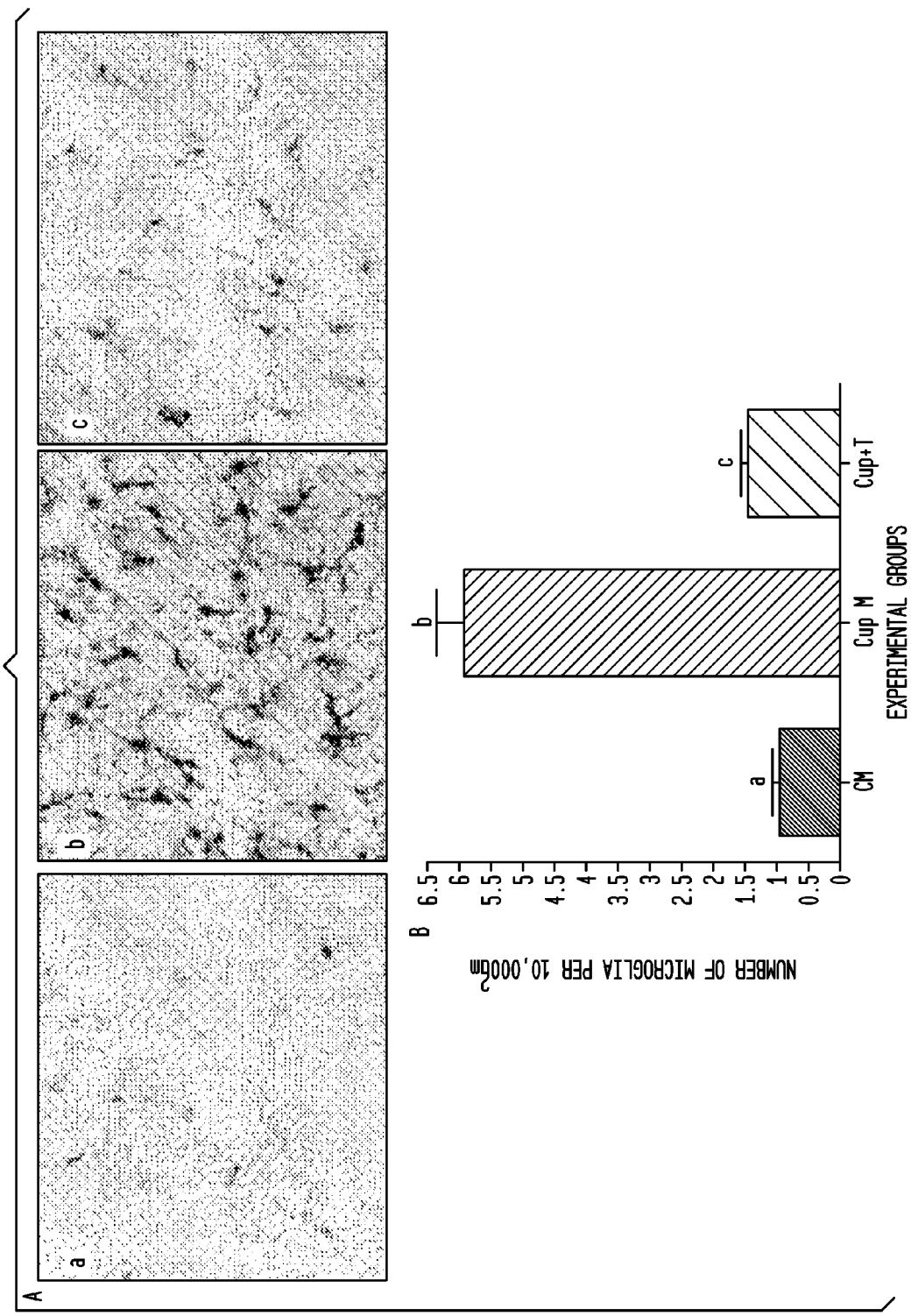

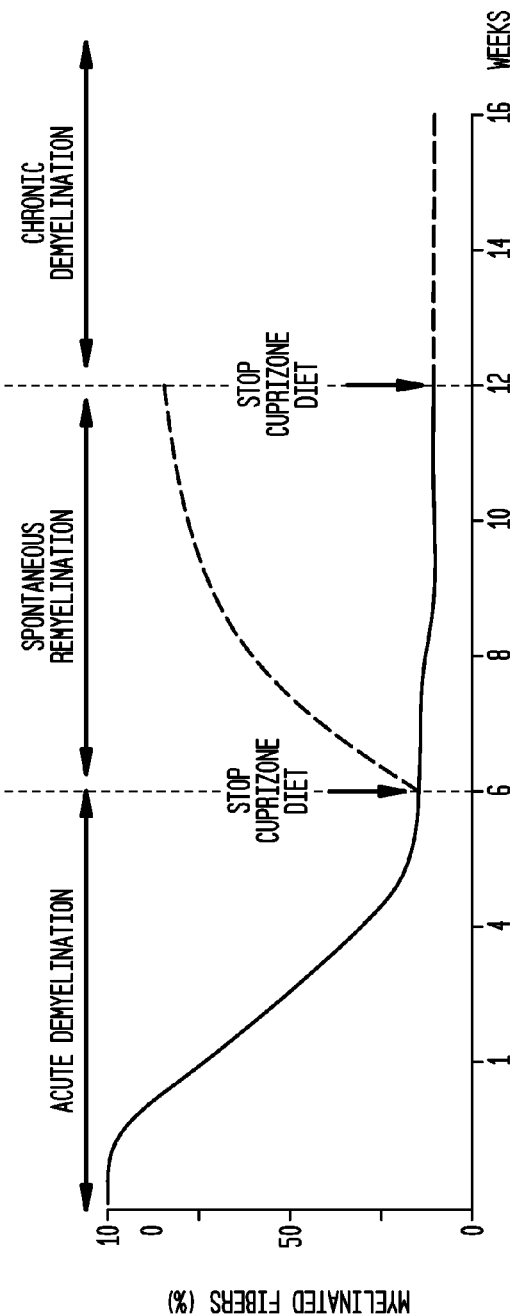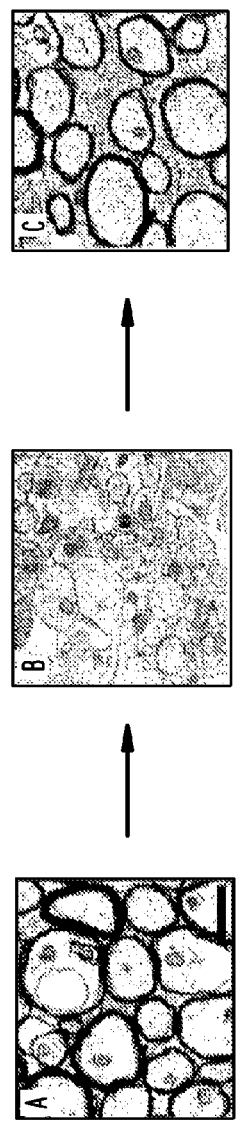
FIG. 4

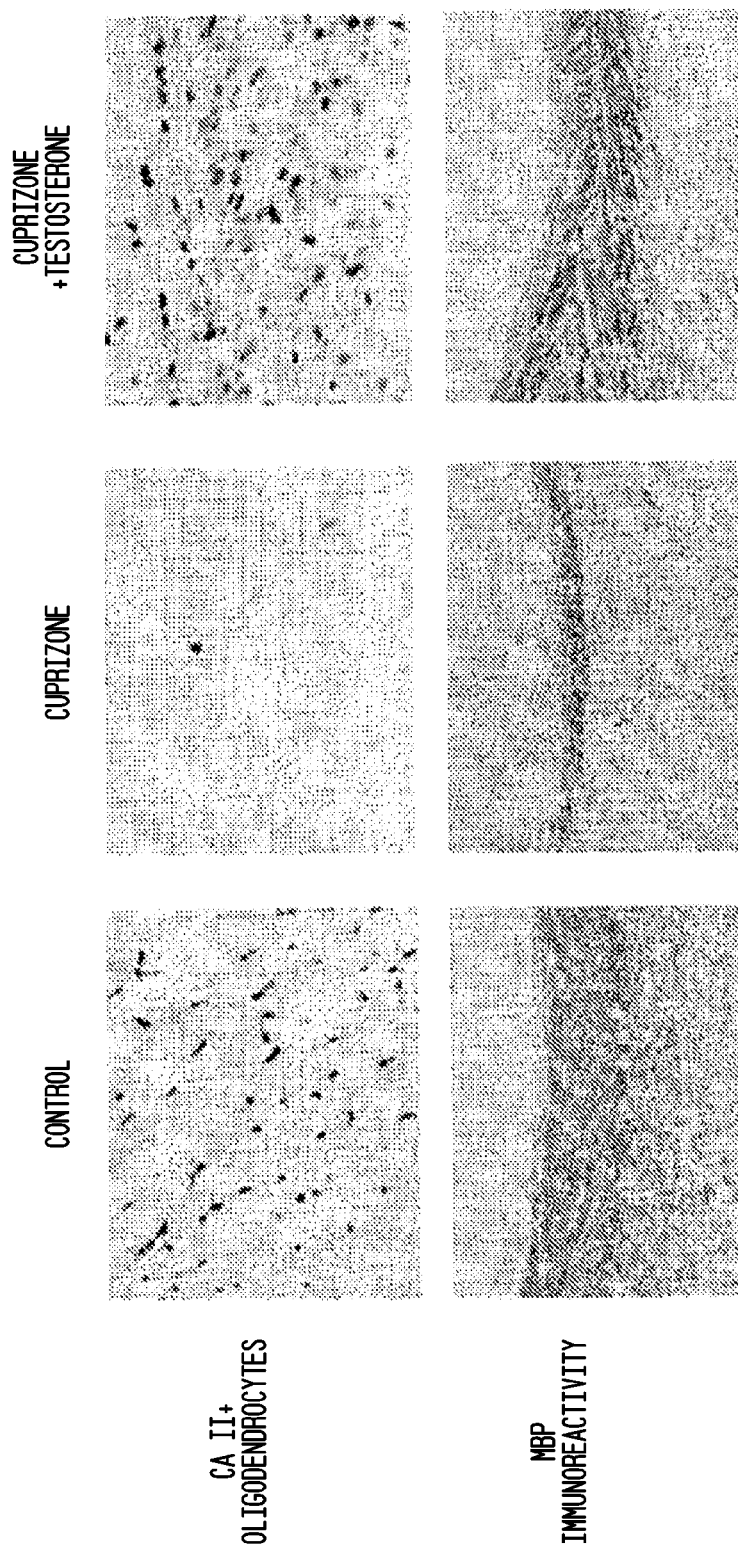

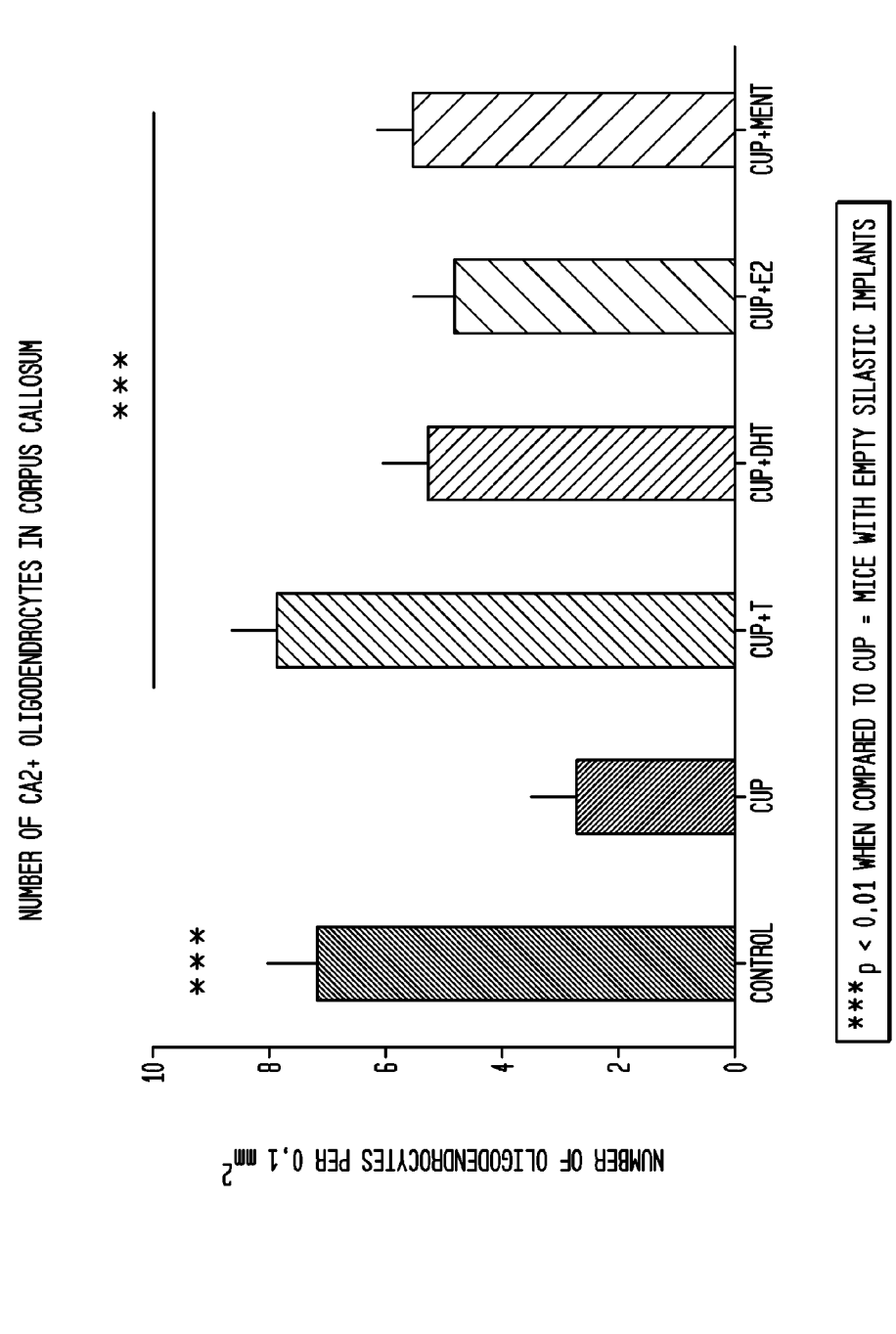

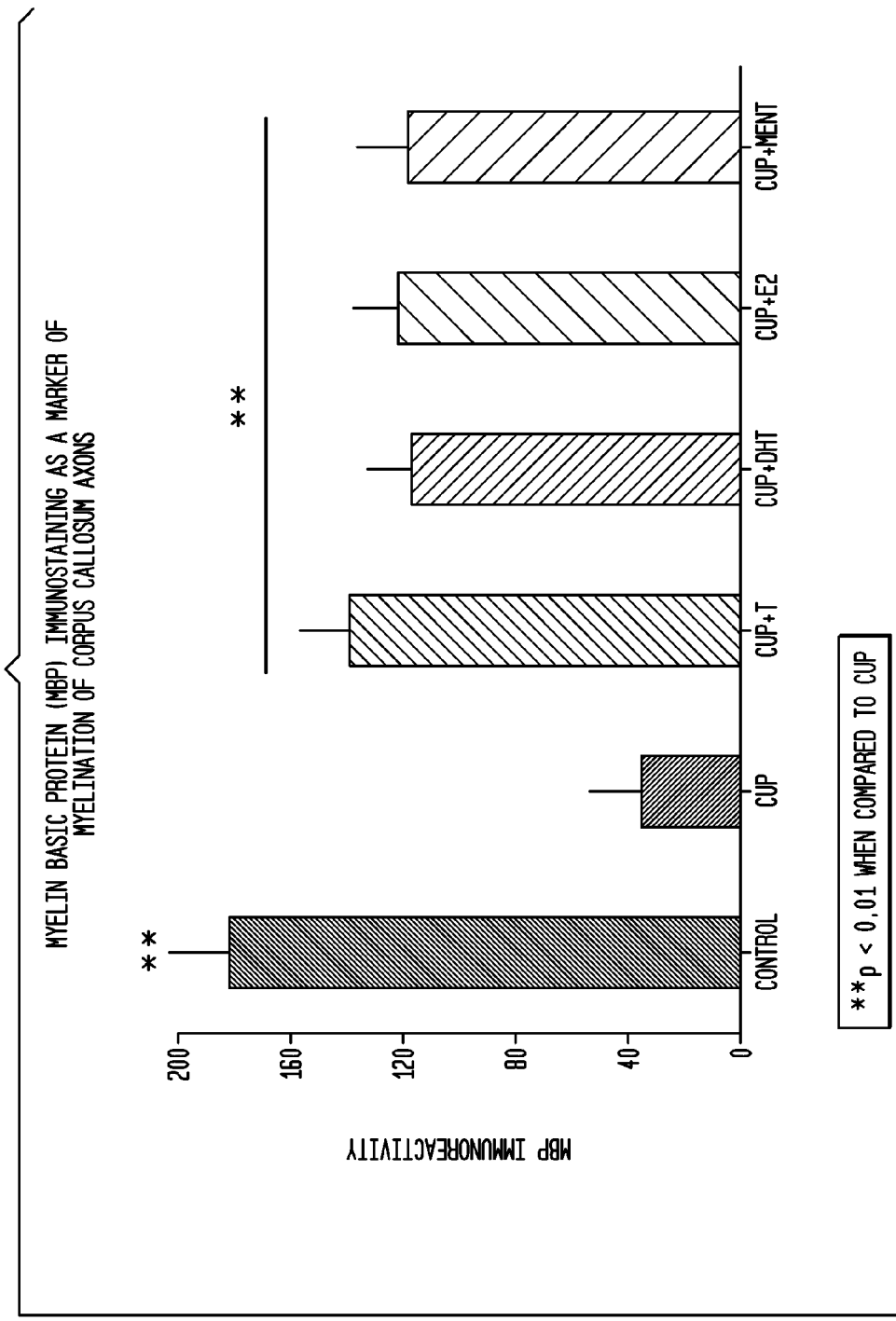

MYELIN REGENERATION WITH ANDROGENS

CROSS-REFERENCE TO RELATED APPLICATIONS

The present application is a national phase entry under 35 U.S.C. §371 of International Application No. PCT/US2012/030041 filed Mar. 22, 2012, published in English, which claims priority from United States Provisional Patent Application No. 61/466,252 filed Mar. 22, 2011, all of which are incorporated herein by reference.

FIELD OF THE INVENTION

The present invention relates to the field of prevention of myelin degeneration and neurodegeneration. More particularly, the present invention relates to myelin repair (remyelination) for the treatment of neurodegenerative diseases such as Multiple Sclerosis (MS).

BACKGROUND OF THE INVENTION

Multiple Sclerosis (MS) is a progressive and disabling disease of the central nervous system (CNS) affecting more than twice as many women as men (1-4). Evidence suggests that neuronal damage begins early in MS (5), with acute axonal injury already present during active demyelination. However, remyelination is known to occur in MS (6,7) where it protects against axon loss (8). Indeed no significant axonal damage can be observed in remyelinated plaques (5). Axons become less receptive to remyelination as MS progresses.

MS is an inflammatory disease in which the fatty myelin sheath around the axons of the brain and spinal chord are damaged leading to demyelination and scarring, as well as a broad spectrum of signs and symptoms. In particular, MS effects the ability of nerve cells in the brain and spinal chord to communicate with each other. When myelin is lost the axons can no longer effectively conduct signals. MS itself effects both male and female patients.

Present pharmacological treatments of multiple sclerosis (MS) are limited to immunomodulatory and anti-inflammatory drugs, which are only palliative and do not significantly slow the progress of the disease (12).

An effective treatment strategy for MS must also include therapeutic agents that reverse axon demyelination in order to prevent irreversible axon loss. Testosterone, a male sex hormone, may have beneficial effects on MS and neuroprotection. (9)

However, stimulating the endogenous capacity of myelin repair has remained an unmet but significant therapeutic need (13). Indeed, myelin can be extensively repaired as part of a natural healing process during early stages of MS, explaining why in most cases the disease starts with a relapsing/remitting course. However, the capacity for myelin repair then progressively decreases, and the disease becomes progressively worse. Moreover, the efficiency of myelin repair markedly differs among patients, and although the prevalence of MS in females is higher compared to that of males, male MS patients generally reach disability milestones earlier than women, and males are associated with more rapid progression of the disease and a worse outcome (14).

7α-methyl-19-nortestosterone (MENT) is a different potent synthetic androgen which does not undergo 5α reduction and has therefore been investigated for long-term clinical use particularly because it is less stimulatory to the prostate. MENT itself has been recognized as useful, for example, in male contraception (10), as well as in maintaining sexual behavior and mood in hypogonadal men (11). MENT has been shown to be 10 to 12 times as active as testosterone on male targets (15). For example, U.S. Pat. No. 6,767,902 discloses methods of male contraceptive by administering MENT and its pharmaceutically acceptable salts, preferably as the sole sperm suppressive agent administered to males for this purpose.

Another known androgen is 5α-dihydrotestosterone or DHT. Indeed, DHT has about three times greater affinity for androgen receptors than does testosterone. DHT is possibly best known for its roles in causing male pattern hair loss and prostate problems. Another known androgen metabolite is estradiol, primarily known as the predominant sex hormone present in females. However, it is also present in males and is a metabolite product of testosterone.

Moreover, estrogens have previously been documented to have neuroprotective and anti-inflammatory effects in experimental models of MS (17). In addition, it has also been discovered that androgen therapy may also offer therapeutic benefits for diseases of myelin other than MS, in particular for leukodystrophies (18).

SUMMARY OF THE INVENTION

In accordance with the present invention, methods for remyelination of a patient have been discovered comprising treating a patient suffering from demyelination with a pharmaceutically effective dosage of an androgen receptor ligand which exerts binding to androgen receptors in order to repair at least part of the demyelination. In a preferred embodiment, the androgen receptor ligand is selected from testosterone, 7α-methyl-19-nortestosterone and its derivatives, and 5α-dehydrotestosterone.

In accordance with one embodiment of the method of the present invention, the androgen receptor ligand comprises MENT in the form of an implant for subcutaneous implantation, and the dosage comprises between about 400 and 2,000 µg/day.

In accordance with another embodiment of the method of the present invention, the androgen receptor ligand comprises MENT and the pharmaceutically effective dosage comprises the MENT in the form of a gel in a dosage comprising between about 12 and 16 mg/g.

In accordance with another embodiment of the method of the present invention, the androgen receptor ligand comprises testosterone, and the pharmaceutically effective dosage comprises the testosterone in the form of a gel including between about 5 and 10 mg.

In accordance with a preferred embodiment of the present invention, the patient comprises a male patient.

In accordance with another embodiment of the method of the present invention, the pharmaceutically effective dosage includes an estrogen receptor ligand which exerts binding to estrogen receptors. Preferably, the estrogen receptor ligand comprises estradiol.

In accordance with another embodiment of the method of the present invention, the pharmaceutically effective dosage includes a progestin compound. Preferably, the progestin compound comprises Nestorone®. In a preferred embodiment, the Nestorone® is present in an effective dosage of 5 mg/day or less. In one embodiment the progestin compound is selected from 16-methylene-17α-acetoxy-19-norpregn-4-ene-3,20-dione (Nestorone®), 18-methyl Nestorone®, nomegestrol acetate, trimegestone, norgestimate, dienogest, drospirenone, chlormadinone acetate, promegestone, retroprogesterone, and 17-hydroxyprogesterone.

In accordance with the present invention, a method for remyelination of a patient has been discovered comprising treating the patient suffering from demyelination with a pharmaceutically effective dosage of an estrogen receptor ligand which exerts binding to estrogen receptors in order to repair at least part of the demyelination. In a preferred embodiment, the estrogen receptor ligand is selected from 17β-estradiol and 17α-estradiol. Preferably, the patient comprises a woman, the estrogen comprises estradiol, and the pharmaceutically acceptable dosage comprises between about 20 µg and 2 mg/d.

In accordance with the present invention, a method for treating MS has also been discovered comprising treating a patient suffering from MS with a pharmaceutically effective dosage of an androgen receptor ligand which exerts binding to androgen receptors in order to effect at last partial remyelination of the patient. In a preferred embodiment, the androgen receptor ligand is selected from testosterone, MENT and its derivatives, and 5α-dehydrotestosterone. Preferably, the androgen receptor ligand comprises MENT. In a preferred embodiment, the MENT is in the form of a subcutaneous implant containing between about 400 and 2,000 µg/day of the MENT. In another embodiment, the MENT is in the form of a gel, comprising from about 12 to 16 mg/g of the MENT.

In one embodiment of the method of the present invention, the androgen receptor ligand comprises testosterone. In a preferred embodiment, the testosterone is in the form of a gel comprising from about 5 to 10 mg of the testosterone.

In a preferred embodiment of this method of the present invention, the patient comprises a male patient.

In accordance with the present invention, it has now been discovered and demonstrated that certain androgen receptor ligands, including testosterone, 7α-methyl-19-nortestosterone, 5α-dihydrotestosterone, and certain estrogen receptor ligands, such as estradiol, have highly beneficial effects on remyelination. These androgen and estrogen receptor ligands (steroids) have thus been shown to have even more beneficial effects on remyelination in in vitro models than had been expected. Testosterone, for example, has been shown to have very strong promyelinating effect in vivo, after demyelination induced by cuprizone intoxication, as well as in vitro on organotypic cultures of cerebellar slices. These pro-myelinating effects of testosterone have been observed in both male and female animals. It is apparent that this promyelinating effect clearly involves the androgen receptor, since it is mimicked by 5α-dihydrotestosterone (DHT), and has been shown to be lost in transgenic mice subsequent to central nervous-specific inactivation of the androgen receptor using CreloxP technology, and furthermore since it is not observed in testicular feminized mice which are thus totally insensitive to androgen because of a mutation in the androgen receptor gene. Finally, this promyelinating effect is also observed with 7α-methyl-19-nortestosterone (MENT) and other androgen binding to the androgen receptor which does not interact with 5α-reductase, as is the case with testosterone, which converts into DHT under this enzyme action.

It has also been shown that testosterone promotes the proliferation and maturation of oligodendrocyte progenitors, and that testosterone also regulates microglial responses and astrogliosis: the number of reactive microglial cells and astrocytes, both of which are markers of neuroinflammation and brain tissue damage, return to normal levels after treatment with testosterone as compared to control experiments.

In addition, testosterone has also been shown to promote remyelination in a model of demyelination induced by the stereotaxic infusion of lysolecithin in the mouse spinal cord, which is a primary target for MS attacks. In this model, the promyelinating effects of testosterone are lost in the CNS in ARKO mice and in testicular feminized mice which lack the androgen receptor, and can be mimicked by MENT. In this model, testosterone treatment is associated with improved functional outcomes.

Using a cuprizone model, estradiol has also been shown to exert promyelinating effects, and testosterone loses its efficiency in aromatase knockout mice. It is thus apparent that both androgens and estrogens play an important role in this remyelination effect. It is thus significant for the compound MENT, which targets the androgen receptor and converts into an estrogen (7α-methyl estradiol) which interacts with the estrogen receptor.

In accordance with the present invention, the androgen receptor (AR) has been identified as a key therapeutic target for promoting myelin repair. Experimental findings by the inventors have also demonstrated that AR ligands strongly promote the remyelination of axons. AR ligands which also have estrogenic activities may have the best therapeutic potential. The AR ligands include testosterone (which is converted to estradiol by the aromatase enzyme), MENT (which is converted to 7α-methyl-estradiol) and 5α-DHT (which is converted to 5α-androstane-3β,17β-diol (3βAdiol), which strongly binds to estrogen receptor beta (ERβ)) (16). In fact, these experimental findings show that the promyelinating effects of testosterone are strongly reduced in aromatase knockout mice.

BRIEF DESCRIPTION OF THE DRAWINGS

The present invention may be more fully appreciated with reference to the following detailed description, which in turn refers to the Figures wherein:

FIG. 3 is a pictorial and graphical representation showing testosterone regulation of microglial responses and estrogliosis;

FIG. 4 is a graphical and pictorial representation showing demyelination induced by cuprizone;

FIG. 5 is a pictorial and graphical representation of testosterone stimulation of remyelination after cuprizone intoxication;

FIG. 6 is a graphical representation showing the number of oligodendrocytes subsequent to hormonal treatments; and FIG. 7 is a graphical representation showing myelination of corpus callosum axons.

DETAILED DESCRIPTION

Figure 1:
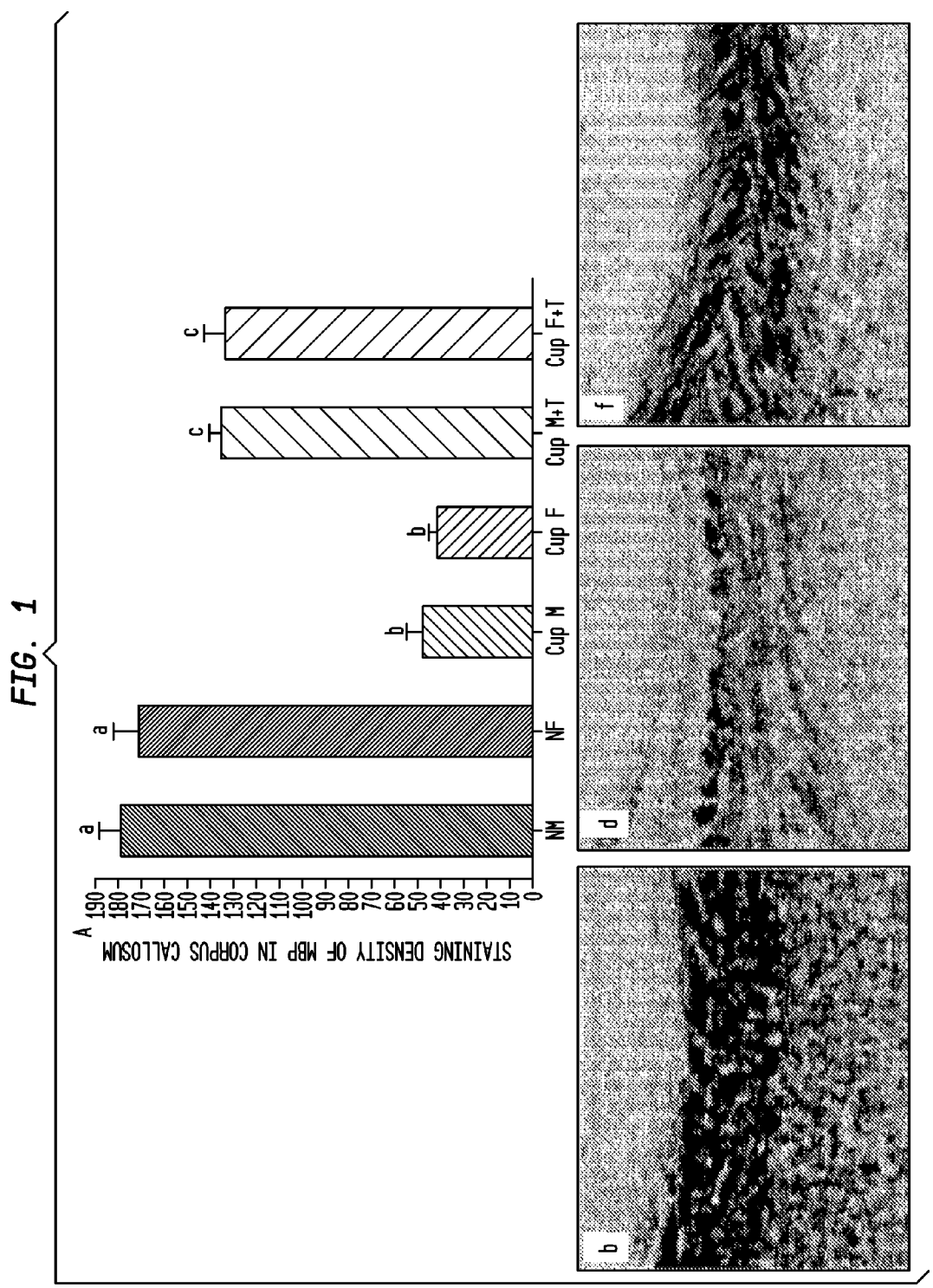
FIG. 1 is a graphical and pictorial view of the staining density of myelin basic protein in corpus callosum of male mice.

The present invention is most particularly based upon the discovery of the particular properties of certain androgens. Most particularly, these androgens exert binding to androgen receptors and elicit androgen-receptor-induced biological responses. These androgens include testosterone, 7α-methyl-19-nortestosterone (MENT), derivatives of MENT, such as fluoro-methyl-19-nortestosterone (eF-MENT), and 5α-dihydrotestosterone (DHT), with MENT being most preferred, and also estrogens, such as estradiol and 7α methyl estradiol.

The androgen receptor ligands and estrogen receptor ligands should be utilized at specific dosage levels. For example, with respect to the androgen receptor ligands, such as MENT, it is preferred that it be utilized at dosage levels of between abut 400 and 2,000 µg/day, preferably at about 1,600 µg/day. These dosages are preferred for use with a subcutaneous implant. However, when used in connection with transdermal application such as with a transdermal gel, it is clearly necessary to utilize greater amounts of the androgen, in this case between about 4,000 and 20,000 µg/day (4 to 20 mg/day), and preferably about 16,000 µg/day (16 mg/day). On the other hand, with an androgen such as testosterone, which is about $1/10$ as active as the MENT, dosages of from about 4,000 to 20,000 µg/day, and preferably about 16,000 µg/day will be required, in the case of subcutaneous implant, and with dosages about 10 times these in the case of transdermal use, as with a transdermal gel composition.

Based on animal experimentation, the mean levels of the following steroids which were induced in the plasma and in the brains of castrated male mice based on subcutaneous silastic implants, in sizes of 5 and 10 mm, as determined by gas chromatography/mass spectrometry, and which induced a myelin response, were as follows:

| IMPLANT | PLASMA LEVEL (ng/ml) | Brain Level (ng/g) |
|---|---|---|
| Testosterone (10 mm) | 3.45 ± 0.40 | 2.37 ± 0.08 |
| 5α-dihydrotestosterone (10 mm) | 0.49 ± 0.11 | 0.96 ± 0.14 |
| Estradiol (5 mm) | 0.39 ± 0.07 | 0.36 ± 0.04 |

In additional experiments, the level of MENT which was induced in the plasma of castrated male mice based on subcutaneous silastic implants, as determined by radioimmunoassay, and which included a myelin response, was as follows:

| SAMPLE NO. | TUBE NOS. | pg/ml | ng/ml (plasma level) |
|---|---|---|---|
| 1 | 80-81 | 1640 | 1.64 |
| 2 | 82-83 | 4200 | 4.20 |
| 3 | 84-85 | 1840 | 1.84 |
| 4 | 86-87 | 1500 | 1.50 |
| 5 | 88-89 | 2020 | 2.02 |
| 6 | 90-91 | 1980 | 1.98 |
| 7 | 92-93 | 2200 | 2.20 |
| 8 | 94-95 | 1580 | 1.58 |

The mean results were 2.12 ng/ml, with a SD of 0.87.

It is, however, within the skill of those in the pharmaceutical art to determine with routine experimentation what dosage of these androgens, such as MENT, and the estrogens, such as estradiol, will be needed, depending on the particular route of administration, to deliver such an effective dose. It is understood that the dosage of androgen, such as MENT, administered in vivo may be dependent on the age, sex, health and weight of the recipient, kind of concurrent treatment, if any, frequency of treatment, and the nature of the pharmaceutical effect desired. The ranges of effective doses provided herein are not intended to be limiting and represent preferred dose ranges. However, the most preferred dosage may be tailored to the individual subject, as is understood and determinable by one skilled in the relevant art. See, e.g., Berkow et al., eds., *The Merck Manual*, 16th Ed., Merck & Co., Rahway, N.J. (1992); Goodman et al., eds., *Goodman and Gilman's The Pharmacological Basis of Therapeutics*, 8th Ed. Pergamen Press Inc., Elmsford, N.Y. (1990); Katzung, *Basic and Clinical Pharmacology*, Appleton & Lang, Norwalk, Conn. (1992); *Avery's Drug Treatment Principles and Practice of Clinical Pharmacology and Therapeutics*, 3rd Ed., ADIS Press Ltd., Williams & Wilkins, Baltimore, Md. (1987); Ebadi, *Pharmacology*, Little, Brown & Co., Boston, Mass. (1985); *Remington's Pharmaceutical Services*, 17th ed., Alphonzo R. Genaro, Mack Publishing Company, Easton, Pa. (1985); which references are entirely incorporated here by reference thereto.

The dosages can be determined by a clinician using conventional dose escalation studies. It can be expected to be within the above preferred ranges. Furthermore, while this discussion has specifically referred to the highly significant androgen component of the present invention, it can, of course, also apply with equal force to the estrogen metabolite hereof.

In addition, by the term "pharmaceutically effective" it is meant that amount which is sufficient to effect the desired changes in the subject. The amount will vary depending upon such factors as the potency of the particular drug, the desired therapeutic effect, and the time span for which the method of application is intended to provide treatment. Those skilled in the pharmaceutical arts will be able to determine both toxic levels and the minimum effective doses of the drug in accordance with standard procedures. In vitro diffusion of the drug from a delivery device of the present invention may be determined, for example, by the methods disclosed in Chien et al., *J. Pharm. Sci.*, 63, 365 (1974) or by the methods described in U.S. Pat. No. 3,710,795, the disclosures of which are incorporated by reference herein.

The specified androgen compounds of this invention can be applied in various ways, both orally and preferably non-orally, including gels, patches, or the like, in a wide range of dosages, ranging broadly from as low as about 400 µg/day and up to about 2,000 µg/day absorbed by the patient, such as by the use of implants and the like, or from about 12 µg/day up to about 16 µg/day gels or the like transdermal systems. Delivery can be either continuous (such as by means of subcutaneous implants) or possibly sequential, such as sequential delivery for from 6 to 8 weeks continuously, followed by 1 to 2 weeks of termination of delivery.

A preferred embodiment of the present invention provides a method for treating MS and obtaining remyelination in a patient suffering from demyelination with a pharmaceutically effective dosage of the androgen MENT at a dosage sufficient to stimulate remyelination. Preferably the amount of MENT utilized will be daily doses of from between about 400 to 2,000 µg/day, preferably about 1,600 µg/day in the form of an implant.

In one embodiment of the present invention, the above compositions are adapted for administration in dosage form for non-oral administration, such as by transdermal administration using gels, sprays, and in the form of subcutaneous implants.

In another embodiment, however, these compositions can be adapted for oral administration, and include other androgens which are active orally such as in the form of tablets, capsules, cachets, dragees, pills, pellets, granules, powder solutions, emulsions, suspensions, and the like.

The applicants have discovered that these specific androgen and estrogen compounds can have unexpected properties in terms of their remyelination and in particular treatment of conditions such as MS.

In accordance with another embodiment of the present invention, it has also been discovered that the combination of the particular androgen receptor ligands and/or estrogen receptor ligands in accordance with the present invention with certain progestin compounds can also be highly beneficial in connection with remyelination. In that regard, reference is made to previously filed International Application No. PCT/US10/53201, which claims the benefit of U.S. Provisional Patent Application No. 61/279,320, filed on Oct. 19, 2009, both of which applications are incorporated herein by reference thereto.

In accordance with these prior applications, it has been disclosed that neurodegeneration in a patient can be treated with a pharmaceutically effective dosage of a progestin compound which exerts binding to progesterone receptors and elicits progesterone-receptor-induced biological responses without interacting with the androgen receptor and without inducing androgen or glucocorticoid biological responses. In particular, the pharmaceutically effective dosage is 5 mg/day or lower whereby neurodegeneration is prevented or reduced. Preferably, the pharmaceutically effective dosage is from about 100 to 400 μg/day and preferably the progestin compound is a compound selected from the group consisting of 16-methylene-17α-acetoxy-19-norpregn-4-ene-3,20-dione (Nestorone®), 18-methyl Nestorone®, nomegestrol acetate, trimegestone, norgestimate, dienogest, drospirenone, chlormadinone acetate, promegestone, retroprogesterone, and 17-hydroxyprogesterone. It has thus been discovered that when combining the progestins of this prior application with the androgen receptor ligands and/or the estrogen receptor ligands of the present invention, further beneficial and unexpected remyelination is obtained.

In order to observe the effects of testosterone treatment on remyelination, demyelination was first achieved by cuprizone treatment, and mice were then implanted with subcutaneous silastic implants of testosterone for a six-week period. The staining density of myelin basic protein in corpus callosum of male mice is shown in FIG. 1.

Strong remyelination was thus observed in mice treated with testosterone for 6 weeks, while none of the untreated mice recovered their myelin. NM (control castrated males), Cup M (cuprizone-treated males receiving empty implants), Cup M+T (cuprizone-treated males after testosterone treatment), NF (control overariectomized females), Cup F (cuprizone-treated females receiving empty implants), Cup F+T (cuprizone-treated females after testosterone treatment) are shown therein. The results demonstrate that there is a strong promyelin aiding effect of testosterone in both male and female mice demonstrated therein. In Figures b, d and f, are shown representative images of immunostaining of mouse corpus callosum with anti-MBP antibody. Thus in image b, myelin staining in a control mouse is shown; in image d, cuprizone treatment for 12 weeks is shown to cause strong demyelination of corpus callosum with little remyelination in the absence of testosterone treatment. Finally, in image f, testosterone treatment for six weeks is shown to promote corpus callosum remyelination after cuprizone intoxication.

Figure 2A:
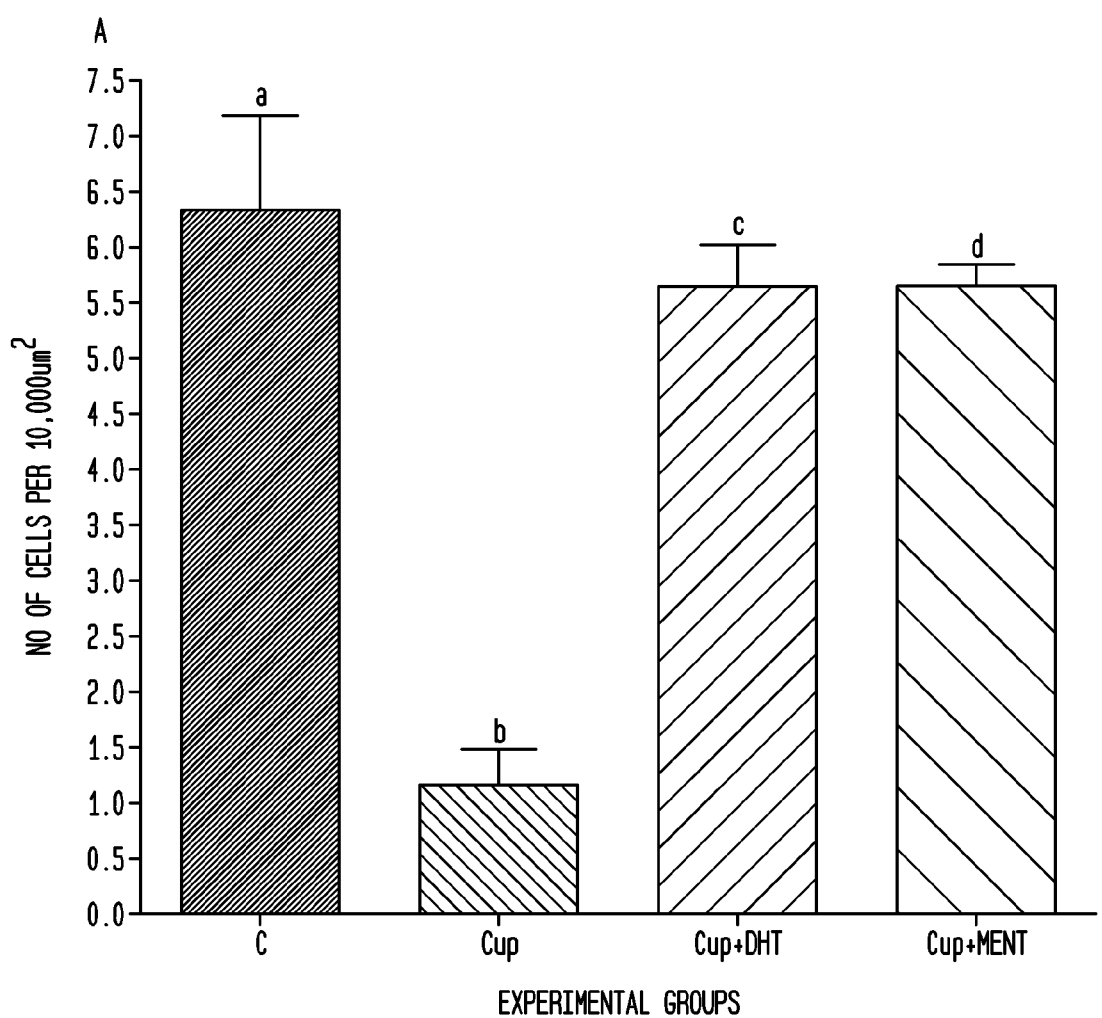
FIG. 2A is a graphical representation showing treatment with 5α-dihydrotestosterone or with 7α-methyl-19-nortestosterone after cuprizone intoxication providing myelination.
Figure 2B:
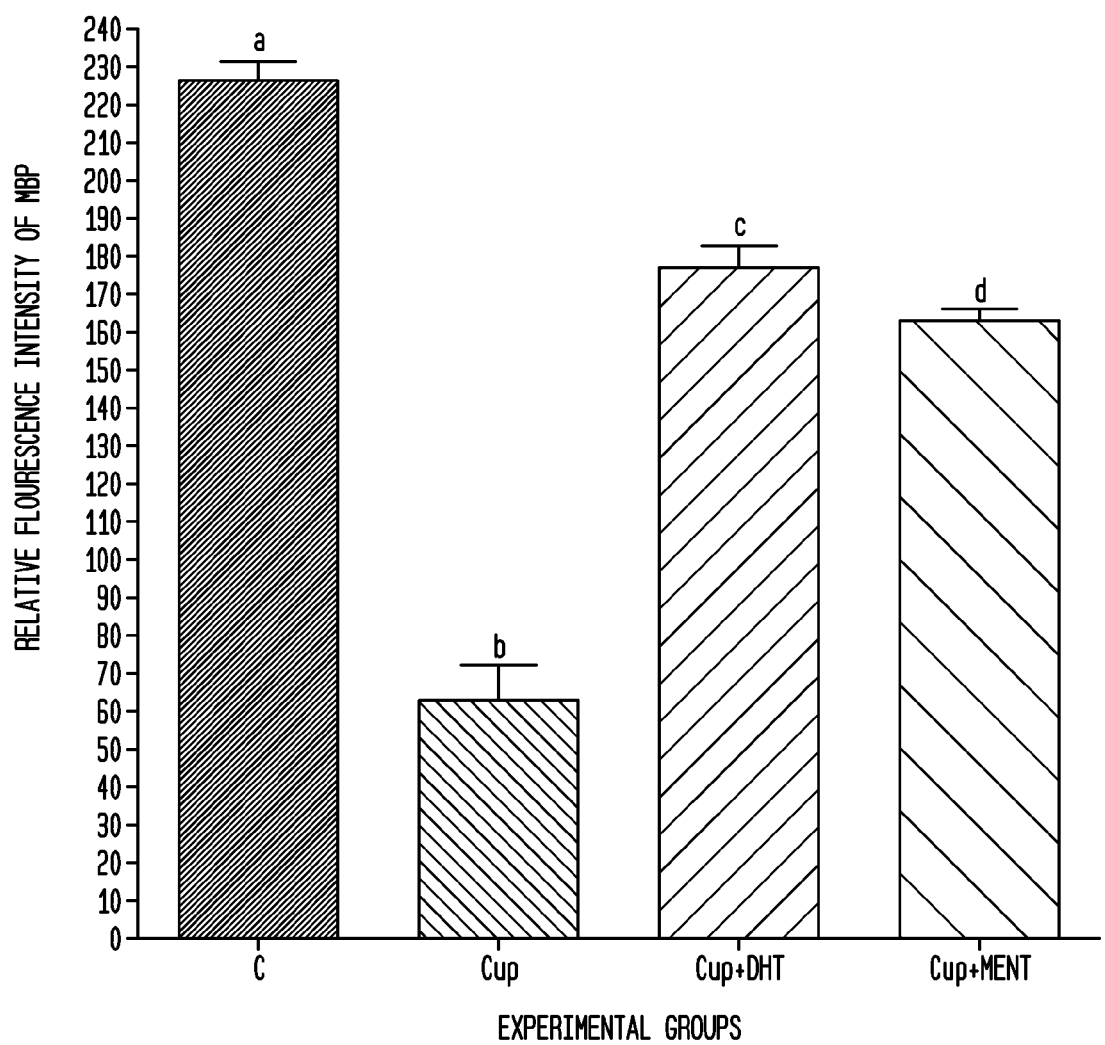
FIG. 2B is a graphical representation showing the intensity of myelin basic protein staining.

As shown in FIGS. 2A and 2B after treatment with 5α-dehydrotestosterone or with 7α-methyl-19-nortestosterone (MENT) after cuprizone intoxication resulted in promotion of remyelination. As shown in FIG. 2A, the number of CAll+ oligodendrocytes in corpus callosum per 0.01 mm² is shown. As shown in FIG. 2B, the intensity of myelin basic protein staining (C: castrated control males; Cup: after 12 weeks of cuprizone intoxication, Cup+DHT: cuprizone intoxication followed by treatment for 6 weeks with DHT; AND Cup+MENT: cuprizone intoxication followed by treatment for 6 weeks with MENT. It is thus clear that the remyelination effect of testosterone can be mimicked by MENT which is an androgen binding to the androgen receptor, which is about 10 to 12 times more potent than testosterone on Male targets, but which does not interact with the 5α reductase as is the case with DHT (15).

As shown in FIG. 3 as discussed above, testosterone regulates microglial responses and astrogliosis. As shown in FIG. 3A, (a) few activated microglial cells (lba 1 positive cells) were observed in the corpus callosum of control mice (castrated males); (b) after 12 weeks of cuprizone intoxication, the density of activated microglial cells dramatically increased; and (c) 9 weeks of testosterone treatment after cuprizone intoxication significantly decreased the number of activated microglial cells. As shown in FIG. 3B the number of activated microglial cells in castrated males (CM), males intoxicated during 12 weeks with cuprizone (Cop M), and males treated with testosterone for 9 weeks after cuprizone intoxication (Cup+T) demonstrates again that the number of reactive microglial cells and astrocytes returns to normal levels after treatment with testosterone but not with the control experiments.

As demonstrated in FIG. 4, by feeding cuprizone to mice during a 12 week period, the axons of the mouse corpus collosum are clearly demyelinated. Cuprizone as noted is a copper-chelating agent which is toxic for CNS oligodendrocytes but spares axons. In any event, as shown in FIG. 4, after such a long-term cuprizone intoxication, there is no spontaneous remyelination of the corpus collosum axons. However, when the mice are treated with subcutaneous silastic implants of testosterone for periods of from 3 to 6 weeks, after termination of the cuprizone diet corpus collosum fibers are replenished by oligodendrocytes forming new myelin sheaths. Similar results are shown in FIG. 5.

In the following experiments using additional subcutaneous silastic implants, which were implanted at 10 mm for testosterone (T), 5α-dihydrotestosterone (DHT) and MENT and at 5 mm for estradiol (E2), the implants produced high physiological levels of testosterone, DHT and E2 in plasma and brain tissue. In each case after 6 weeks of hormonal treatment following 12 weeks of cuprizone intoxication, the results obtained are shown in FIGS. 6 and 7.

To further demonstrate the mechanism of the remyelination effects obtained with androgen receptors such as testosterone, where the androgen receptor was selectively inactivated in the central nervous system, these remyelinating effects were terminated. In experiments which were conducted in which the central nervous system selective inactivation was carried out by the Cre/lox technology and in testicular feminized mice devoid of functional androgen receptors due to a gene mutation, the remyelinating effects of testosterone were eliminated. Furthermore, in aromatase knockout mice, the remyelinating effects with testosterone were diminished, which suggests that both androgen and estrogen receptors are involved.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

REFERENCES

1. Confavreux C, Aimard G, Devic M. Course and prognosis of multiple sclerosis assessed by the computerized data processing of 349 patients. Brain 1980; 103(2):281-300

2. Confavreux C, Vukusic S. Natural history of multiple sclerosis: a unifying concept. Brain 2006; 129(Pt 3):606-16
3. Pugliatti M, Rosati G, Carton H, Riise T, Drulovic J, Vecsei L, Milanov I. The epidemiology of multiple sclerosis in Europe. Eur. J. Neurol. 2006; 13(7):700-22
4. Dutta R, Trapp B D. Pathogenesis of axonal and neuronal damage in multiple sclerosis. Neurology 2007; 68(22 Suppl 3):S22-S31
5. Kornek B, Storch M K, Weissert R, Wallstroem E, Stefferl A, Olsson T, Linington C, Schmidbauer M, Lassmann H. Multiple sclerosis and chronic autoimmune encephalomyelitis: a comparative quantitative study of axonal injury in active, inactive, and remyelinated lesions. Am. J. Pathol. 2000; 157(1):267-76
6. Patani R, Balaratnam M, Vora A, Reynolds R. Remyelination can be extensive in multiple sclerosis despite a long disease course. Neuropathol. Appl. Neurobiol. 2007; 33(3):277-87
7. Patrikios P, Stadelmann C, Kutzelnigg A, Rauschka H, Schmidbauer M, Laursen H, Sorensen P S, Bruck W, Lucchinetti C, Lassmann H. Remyelination is extensive in a subset of multiple sclerosis patients. Brain 2006; 129(Pt 12):3165-72
8. Irvine K A, Blakemore W F. Remyelination protects axons from demyelination-associated axon degeneration. Brain 2008; 131(Pt 6):1464-77
9. Sicotte N, Giesser B., Tandon V, Klutch R, Steiner B, Drain A, Shattuck D., Hull L, Wang H, Elashoff R, Swerdloff R, Voskuhl R. Testosterone Treatment in Multiple Sclerosis. A Pilot Study. Arch Neurol. 2007; 64(5):683-688
10. Sundaram et al., Ann. Med. 1993 Apr. 25(2):199-205
11. Anderson et al., "7α-methyl-19-nortestosterone maintains sexual behavior and mood in hypogonadal men," J. Clin. Endocrinol. Metab. 1999 October; 84(10):3556-62
12. El-Etr M, Ghoumari A, Sitruk-Ware R, Schumacher M (2010) Hormonal influences in multiple sclerosis: New therapeutic benefits for steroids. Maturitas 68:47-51
13. Franklin R J, FFrench-Constant C (2008) Remyelination in the CNS: from biology to therapy. Nat Rev Neurosci 9:839-855
14. Confavreux C, Vukusic S (2006) Age at disability milestones in multiple sclerosis. Brain 129:595-605.
15. Kumar N., AK Didolkar, C Monder, CW Bardin and K Sundaram. The biological activity of 7 alpha-methyl-19-nortestosterone is not amplified in male reproductive tract as is that of testosterone. *Endocrinology,* 1992; 130; 3677-3683
16. Sugiyama N, Barros R P, Warner M, Gustafsson J A (2010) ERbeta: recent understanding of estrogen signaling. Trends Endocrinol Metab 21:545-552
17. Gold S M, Voskuhl R R (2009) Estrogen and testosterone therapies in multiple sclerosis. Prog Brain Res 175:239-251
18. Dubois-Dalcq M, Feigenbaum V, Aubourg P (1999) The neurobiology of X-linked adrenoleukodystrophy, a demyelinating peroxisomal disorder. Trends Neurosci 22:4-12

The invention claimed is:

1. A method for remyelination of a patient comprising treating said patient suffering from demyelination with a pharmaceutically effective dosage of an androgen receptor ligand which exerts binding to androgen receptors in the form of an implant or a transdermal device, wherein said pharmaceutically effective dosage of said androgen receptor ligand in said implant comprises between about 400 and 2,000 μg/day and said pharmaceutically effective dosage of said androgen receptor ligand in said transdermal device comprises between about 4,000 and 20,000 μg/day in order to repair at least part of said demyelination, said androgen receptor ligand comprising 7α-methyl-19-nortestosterone (MENT).

2. The method of claim 1 wherein said pharmaceutically effective dosage comprises said MENT in the form of a gel.

3. The method of claim 1 wherein said patient comprises a male patient.

4. The method of claim 1 wherein said pharmaceutically effective dosage includes an estrogen receptor ligand which exerts bonding to estrogen receptors.

5. The method of claim 4 wherein said estrogen receptor ligand comprises estradiol.

6. The method of claim 1 wherein said pharmaceutically acceptable dosage includes a progestin compound.

7. The method of claim 6 wherein said progestin compound comprises Nestorone®.

8. The method of claim 7 wherein said Nestorone® is present in an effective dosage of 5 mg/day or less.

9. The method of claim 6 wherein said progestin compound is selected from the group consisting of 16-methylene -17α-acetoxy-19-norpregn-4-ene-3,20-dione (Nestorone®), 18-methyl Nestorone®, nomegestrol acetate, trimegestone, norgestimate, dienogest, drospirenone, chlormadinone acetate, promegestone, retroprogesterone, and 17-hydroxyprogesterone.

* * * * *